US008626265B2

(12) United States Patent
Hempel et al.

(10) Patent No.: US 8,626,265 B2
(45) Date of Patent: Jan. 7, 2014

(54) DEVICE AND METHOD FOR REDUCING THE HEART RATE OF A PATIENT, AND APPARATUS HAVING THE DEVICE

(75) Inventors: Eckhard Hempel, Nürnberg (DE); Stefan Popescu, Erlangen (DE); Nicolae Rusca, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 83 days.

(21) Appl. No.: 13/037,514

(22) Filed: Mar. 1, 2011

(65) Prior Publication Data

US 2011/0218421 A1 Sep. 8, 2011

(30) Foreign Application Priority Data

Mar. 3, 2010 (DE) .......................... 10 2010 010 055

(51) Int. Cl.
*A61B 5/05* (2006.01)

(52) U.S. Cl.
USPC ........... 600/407; 600/409; 600/410; 600/411; 600/437

(58) Field of Classification Search
USPC .................................. 600/407–429, 437–480
See application file for complete search history.

(56) References Cited

U.S. PATENT DOCUMENTS

| 6,853,858 | B2* | 2/2005 | Shalev | 607/3 |
| 7,146,209 | B2* | 12/2006 | Gross et al. | 607/2 |
| 7,684,859 | B2* | 3/2010 | Shalev et al. | 607/2 |
| 7,877,147 | B2* | 1/2011 | Shalev et al. | 607/45 |
| 7,974,697 | B2* | 7/2011 | Maschino et al. | 607/45 |
| 2003/0176892 | A1* | 9/2003 | Shalev | 607/3 |
| 2008/0056547 | A1* | 3/2008 | Kokubun et al. | 382/128 |
| 2010/0137896 | A1 | 6/2010 | Mukhina et al. | |

FOREIGN PATENT DOCUMENTS

| DE | 202004009080 U1 | 9/2004 |
| DE | 102008037348 A1 | 2/2010 |
| EP | 2156816 A2 | 2/2010 |

OTHER PUBLICATIONS

B.J.Schaller, A.Filis, M.Buchfelder, The trigemino-cardiac reflex—The solution of many unresolved problems in medicine?, Journal of Chinese Clinical Medicine vol. 2, Nr. 10, Okt. 2007; Others.
Scott Lang, Dennis T. Lanigan, Mike van der Wal, "Trigeminocardiac reflexes: maxillary and mandibular variants of the oculocardiac reflex", Canadian Journal of Anaesthesia, 1991, 38:6, pp. 757-760; Others.
Schaller B., et al., "Trigeminocardiac reflex during surgery in the cerebellopontine angle", J. Neurosurg., vol. 90, Feb. 1999, S. 215-220; Others; 1999.
German priority application DE 10 2010 010 055.2 filed Mar. 3, 2010 and not yet published.
German Office Action dated Oct. 1, 2010.

* cited by examiner

*Primary Examiner* — Sanjay Cattungal
(74) *Attorney, Agent, or Firm* — Harness, Dickey & Pierce, P.L.C.

(57) ABSTRACT

A device is disclosed for stimulating the trigeminal nerve of a patient in order to reduce the heart rate of the patient for recording image information from the heart of the patient. In at least one embodiment, the device includes at least one device for mechanical, electrical, magnetic, thermal, optical and/or chemical stimulation of the trigeminal nerve. Furthermore, at least one embodiment relates to an apparatus including at least one such device and a unit for registering the heart rate of the patient, which unit interacts with the device. Furthermore, at least one embodiment moreover relates to a method for reducing the heart rate of a patient in order to record image information from the heart of the patient, in which method the trigeminal nerve of the patient is stimulated by at least one such device in order to lower the heart rate of the patient.

26 Claims, 2 Drawing Sheets

DEVICE AND METHOD FOR REDUCING THE HEART RATE OF A PATIENT, AND APPARATUS HAVING THE DEVICE

PRIORITY STATEMENT

The present application hereby claims priority under 35 U.S.C. §119 on German patent application number DE 10 2010 010 055.2 filed Mar. 3, 2010, the entire contents of which are hereby incorporated herein by reference.

FIELD

At least one embodiment of the invention generally relates to a device and/or to a method for reducing the heart rate of a patient, and/or to an apparatus having such a device.

BACKGROUND

Patients suffering from cardiac disorders are subjected to e.g. scans by X-ray computed tomography scanners, provided this is necessary from a medical point of view and sensible for examining the heart, wherein a scan is understood to mean the recording of a multiplicity of 2D X-ray projections, from different projection directions, of the heart, usually whilst the heart or the patient is advanced relative to the X-ray recording system of the X-ray computed tomography scanner. The aim of the examination is the generation of high-quality and meaningful images of the heart, which often form the basis for a diagnosis.

Since the heart is a moving organ, every effort is made in the reconstruction of slice images and 3D images of the heart (which are created on the basis of the recorded 2D X-ray projections) that only those 2D X-ray projections recorded during the cardiac phase of the cardiac cycle of the patient in which the heart, where possible, was not going through any motion are used, in particular to avoid movement artifacts in the reconstructed slice images and 3D images of the heart. Here it is conventional for an electrocardiogram (EKG) of the heart of the patient to be recorded for establishing the cardiac cycle of the heart of the patient.

In order to increase the quality of generated images of the heart of a patient, it is desirable to lower the heart rate or the cardiac frequency of the heart of a patient when recording the 2D projections, as a result of which it is possible to lengthen the phase during which the heart and the blood vessels of the heart exhibit practically no motion. By way of example, the heart rate can be lowered by administering beta blockers; however, like any other medicament, these have side effects that should be avoided where possible. A further disadvantage of beta blockers is that their effect only sets in approximately 30 minutes after being taken, and so, undesirably, there can be waiting periods before the recording of the 2D projections is started.

SUMMARY

In at least one embodiment of the invention, a device, an apparatus and/or a method is specified such that the heart rate of a patient can be reduced without administering a medicament in order to record image information from the heart of the patient.

According to at least one embodiment of the invention, a device is disclosed for stimulating the trigeminal nerve of a patient in order to reduce the heart rate of the patient for recording image information from the heart of the patient, having means for mechanical, electrical, magnetic, thermal, optical and/or chemical stimulation of the trigeminal nerve.

The trigeminal nerve is the fifth cranial nerve of a human and is part of the parasympathetic nervous system, which is also referred to as the "rest and digest system", since it ensures rest, relaxation and protection of the body. The trigeminal nerve's name is a result of its division into three parts or its three main branches, of which one runs to the eye, one runs to the maxilla and one runs to the mandible of a human. The so-called oculocardiac reflex was discovered as early as 1908 by Dagini and Aschner. It occurs if pressure is exerted on the eyeball, which stimulates the branch of the trigeminal nerve running to the eye, whereupon the organism reacts by lowering the heart rate or the cardiac frequency. Nowadays, the reflex is also referred to as the trigemino-cardiac reflex (TCR). The reflex lowers the mean arterial blood pressure and the heart rate by more than 20% compared to the baseline values of a human before the stimulation of the trigeminal nerve.

The inventors have recognized that the trigemino-cardiac reflex can be used to lower the heart rate of a patient when recording image information from the heart of the patient, more particularly to lengthen the cardiac phase during which the heart and the blood vessels of the heart exhibit practically no motion. Therefore, in at least one embodiment the inventors propose a device by which the trigeminal nerve of a patient can be stimulated by at least one mechanical device/method, for example by applying pressure, by at least one electrical device/method, for example by applying an electric current, by at least one thermal device/method, for example by applying heat or cold, by at least one magnetic device/method, by at least one optical device/method and/or by at least one chemical device/method. The stimulation can be brought about either by using only one of the aforementioned options or by using any combinations of the aforementioned options for stimulation.

An embodiment of the invention provides for the device to comprise at least one device for exerting pressure on the trigeminal nerve, which device may include at least one elastic balloon, which can be filled with a medium and is intended to be arranged on an eye of the patient in order to stimulate the branch of the trigeminal nerve running to the eye by exerting pressure on the eye or the eyeball. In general, provision is made in each eye for one balloon has been fitted to the size of an average human eye such that the trigeminal nerve can be stimulated on both sides in order to lower the heart rate.

A development of the embodiment provides for the at least one balloon to be arranged on spectacles that can be worn by the patient. Rather than spectacle lenses, the spectacle frame is preferably provided with a balloon on both sides. The spectacles can be provided with ear clips and is preferably fixed to the head of the patient by means of an elastic back-of-the-head securing band.

According to a further embodiment of the invention, the at least one device/method for exerting pressure on the trigeminal nerve have at least one pump for the medium, controllable valves for the flow of medium into and from the at least one balloon, at least one pressure sensor for establishing the pressure in the balloon and/or a control unit for actuating the at least one pump. The medium can be a liquid or, preferably, a gaseous medium, e.g. air. Each balloon preferably has a controllable valve for the flow of medium into the balloon and a controllable valve for the flow of medium from the balloon in order to produce a certain pressure in the balloon, which pressure can be measured by a pressure sensor.

According to one variant of at least one embodiment of the invention, the device comprises at least one device for applying electric current to the trigeminal nerve, which device includes at least one pair of electrodes that can be attached to the facial skin of the patient, at least one current generator that can be connected to the at least one pair of electrodes and/or a control for actuating the current generator. One pair of electrodes is preferably provided for each half of the face, with each pair of electrodes being arranged on a cheek of a patient such that each electrode is situated over the branch of the trigeminal nerve running to the maxilla and/or the branch of the trigeminal nerve to the mandible. The electric circuit resulting during the operation of a pair of electrodes then stimulates the trigeminal nerve directly.

According to a further variant of at least one embodiment of the invention, the current generator is a power-pulse-current generator for generating a succession of current pulses. The shape, the amplitude, the duration and/or the repetition rate of the current pulses can preferably be set in the power-pulse-current generator such that rectangular current pulses, saw-tooth current pulses, current pulses with elliptical edges or other types of current pulses can be generated for stimulating the trigeminal nerve and lowering the heart rate.

Another embodiment of the invention provides for the device to have at least one device for acupressure, e.g. at least one pressure cushion that can be filled with a medium, for mechanically stimulating the trigeminal nerve, and/or at least one device for acupuncture, e.g. at least one acupuncture needle, for stimulating the trigeminal nerve.

Here, the acupuncture needles can be placed onto the face of the patient such that the trigeminal nerve, more particularly the branch of the trigeminal nerve running to the mandible and/or the branch of the trigeminal nerve running to the maxilla, is stimulated mechanically. A current can additionally be applied to the acupuncture needles, as in electro-acupuncture, in order also to simulate the trigeminal nerve by electrical means. To this end, use can be made of the aforementioned power-pulse-current generator and the aforementioned control for actuating the power-pulse-current generator.

Special acupuncture needles also allow thermal stimulation of the trigeminal nerve. Thus, acupuncture needles can be heated in a targeted fashion, whether by electrical-current control or by providing each acupuncture needle with a flammable medium that heats the acupuncture needle by combustion. Such acupuncture needles are also known as moxibustion needles. Thermal stimulation of the trigeminal nerve can also be achieved by using an infrared laser for laser acupuncture or by burning herbs, e.g. common wormwood, on or in the vicinity of the skin for thermal acupuncture.

Alternatively, acupuncture needles can be designed as cannulae, and so a chemical substance can be supplied in a controlled fashion via the cannulae, by which chemical substance the trigeminal nerve is chemically stimulated.

Magnetic stimulation of the trigeminal nerve is also possible, e.g. by using permanent magnetic substances that are applied to the skin, which is understood to mean a type of magnetic acupuncture.

A further option for stimulation lies in the photic or optical stimulation by way of laser light, which is understood to mean another type of laser acupuncture.

Moreover, the aforementioned pressure cushions can, alternatively or additionally, be arranged on the face, for example by using a mask, such that pressing movements, initiated in a targeted fashion, on the trigeminal nerve stimulate the trigeminal nerve (again, preferably, the branch of the trigeminal nerve running to the mandible and/or the branch of the trigeminal nerve running to the maxilla), for example by increasing the amount of medium in each pressure cushion in a pulsed fashion from time to time. Here use can be made of the device used for the eyes, more particularly the pump, the valves and the control unit.

At least one embodiment of the invention is also directed to an apparatus including at least one device as described above for stimulating the trigeminal nerve and a unit for registering the heart rate of the patient, preferably for operating the device according to the heart rate of the patient, which unit interacts with this device or is connected thereto. The unit for registering the heart rate of the patient can be an EKG instrument that registers the activity of the heart of the patient. The trigeminal nerve can be stimulated accordingly by the respective control, based on the activity of the heart, in particular the heart rate of the patient, in a feedback loop e.g. to the control unit for actuating the pump or the control for actuating the power-pulse-current generator.

According to one development of at least one embodiment of the invention, the apparatus has an imaging instrument connected to the unit for registering the heart rate of the patient such that the image information is preferably recorded when the heart rate of the patient has been lowered by stimulating the trigeminal nerve of the patient.

In doing so, variants of at least one embodiment of the invention provide for the imaging instrument to be an X-ray computed tomography scanner, a C-arm X-ray scanner or a magnetic resonance imaging scanner.

At least one embodiment of the invention is moreover directed to a method for reducing the heart rate of a patient in order to record image information from the heart of the patient, in which method the trigeminal nerve of the patient is stimulated by at least one of the above-described devices in a targeted fashion in order to lower the heart rate of the patient.

The trigeminal nerve is preferably stimulated in a mechanical, electrical, thermal, magnetic, optical and/or chemical fashion.

Variants of at least one embodiment of the invention provide for the trigeminal nerve to be stimulated in a targeted fashion by pressure being exerted on at least one eye of the patient by way of a balloon filled with a medium and/or by applying current pulses to the trigeminal nerve and/or by stimulating the trigeminal nerve with at least one device/method for acupuncture.

The heart rate of the patient preferably is monitored by a unit for registering the heart rate of the patient during the stimulation of the trigeminal nerve and image information from the heart of the patient is recorded by an imaging instrument during the stimulation of the trigeminal nerve.

BRIEF DESCRIPTION OF THE DRAWINGS

An example embodiment of the invention is illustrated in the attached schematic drawings, in which.

DETAILED DESCRIPTION OF THE EXAMPLE EMBODIMENTS

Figure 1:
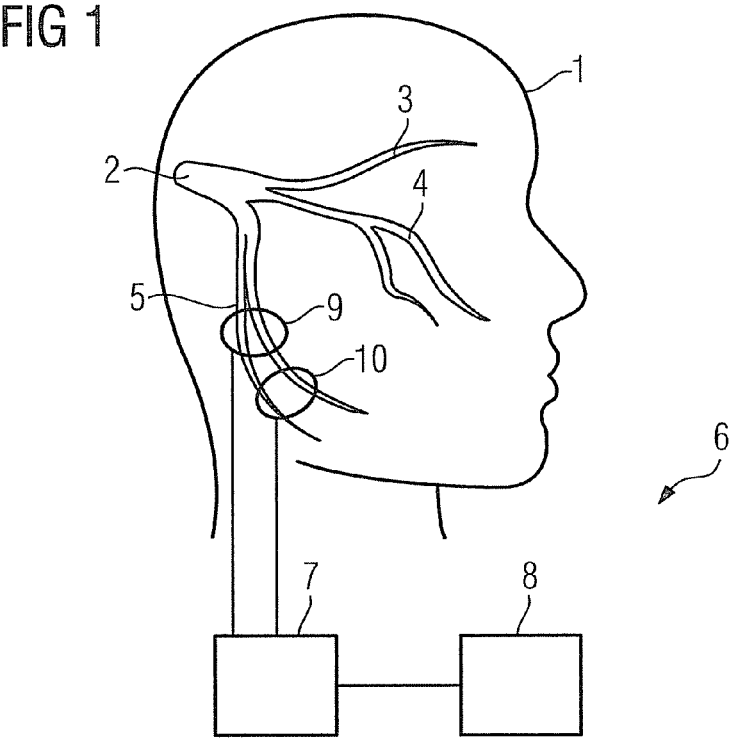
FIG. 1 shows a device for stimulating the trigeminal nerve of a patient by applying current pulses to the trigeminal nerve.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 illustrates a first example embodiment of a device for stimulating the trigeminal nerve of a human, as a result of which the heart rate in a human can be lowered. In this context, the head 1 of a human with the course of the trigeminal nerve has been illustrated schematically. As already mentioned at the outset, the trigeminal nerve has three main branches, of which the first main branch 3 runs to the eye, the second main branch 4 runs to the maxilla and the third main branch 5 runs to the mandible of a human.

In the present example embodiment of the invention, current pulses are applied by way of the device 6 illustrated in FIG. 1 to the third main branch 5 of the trigeminal nerve running to the mandible in order to stimulate and thereby trigger the trigemino-cardiac effect that lowers the heart rate. To this end, the device 6 has a power-pulse-current generator 7.

In the case of the present example embodiment of the invention, there is a separately embodied control 8 for actuating the power-pulse-current generator 7; however, the control can also be part of the power-pulse-current generator 7, i.e. an integral component of the power-pulse-current generator 7. A pair of electrodes 9, 10 is connected to the power-pulse-current generator 7 in the case of the present example embodiment of the invention. As illustrated in FIG. 1, the electrodes 9, 10 can be applied to the cheek of a human, with the electrodes being arranged over the course of the third main branch 5 of the trigeminal nerve.

The power-pulse-current generator 7 can generate successions of current pulses for stimulating the trigeminal nerve, which pulses can be set in respect of their shape, amplitude, duration and/or repetition rate.

A second device 6 of this type can also be provided for the other half of the face (not illustrated in FIG. 1) of a human in order also to stimulate the third main branch of the trigeminal nerve running in the other half of the face.

As an alternative, an array of electrodes can be provided in each case instead of a pair of electrodes provided for a half of the face, which array can be connected to a plurality of current generators for producing similar or different successions of current pulses.

Figure 2:
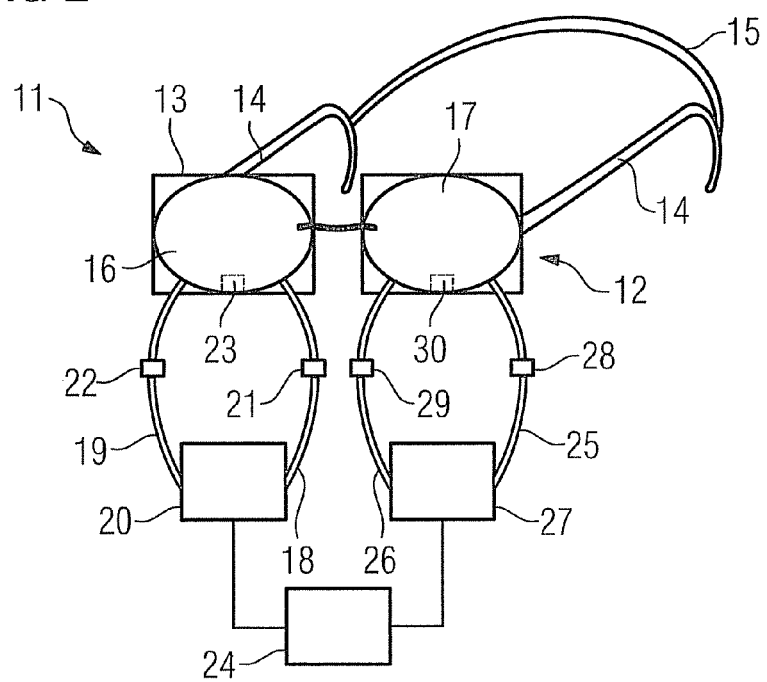
FIG. 2 shows a device for stimulating the trigeminal nerve of a patient by applying pressure to the eyeballs of a human.

FIG. 2 shows a second example embodiment of a device 11 for stimulating the trigeminal nerve, which device is used to stimulate the trigeminal nerve by applying mechanical pressure. The main branch of the trigeminal nerve running to the eye of a human is stimulated in this case by applying pressure to the eyeball of an eye.

The device 11 shown in FIG. 2 comprises spectacles 12 that can be worn by a human, which spectacles have a spectacle frame 13 with clips 14 and an elastic back-of-the-head securing band 15 in the current example embodiment of the invention. Instead of spectacle lenses, the spectacle frame 13 in each case has an elastic balloon 16, 17, which can be filled with a medium, for each eye. The medium is air in the case of the present example embodiment of the invention.

The balloon 16 is connected to a compressed-air pump 20 via an inlet line 18 and an outlet line 19. There is a controllable valve 21 in the inlet line 18 and there is a controllable valve 22 in the outlet line 19. Moreover, a pressure sensor 23 is associated with the balloon 16. The compressed-air pump 20 is connected to a control unit 24 for controlling the pressure in the balloon 16. The controllable valves 21, 22 and the pressure sensor 23 are likewise connected (not illustrated) to the control unit 24.

The balloon 17 is accordingly connected to a second compressed-air pump 27 via an inlet line 25 and an outlet line 26. There is a controllable valve 28 in the inlet line 25 and there is a controllable valve 29 in the outlet line 26. The balloon 17 also has an associated a pressure sensor 30. The compressed-air pump 27, the controllable valves 28, 29 and the pressure sensor 30 are connected to the control unit 24 that controls the pressure in the balloon 17.

In order to stimulate the main branch of the trigeminal nerve running to the eye, the spectacles 12 are put on a patient and fixed using the back-of-the-head securing band 15. Air for elastic expanding of the balloons 16, 17, and, hence, for exerting pressure on the eyeballs of the patient and thus, indirectly, for exerting pressure on the trigeminal nerve, can then be supplied to the elastic balloons 16, 17 in a targeted fashion, inter alia by the compressed-air pumps 20, 27; this is controlled by the control unit 24. In the process, the pressure in the balloons 16, 17 is continuously monitored by the pressure sensors 23 and 30. Incidentally, the flow of air into and from the balloons 16, 17 is controlled not only by the compressed-air pumps 20, 27, but also by the controllable valves 21, 22 and 28, 29, wherein there can also be closed-loop control of the respective pressure.

The control unit 24 has (not illustrated) an emergency-off switch, a digital pressure display for the pressures prevailing in the balloons 16, 17, LED displays for the function of the controllable valves 21, 22, 28, 29 and LED displays for the function of the compressed-air pumps 20, 27, with green LEDs signaling normal operation and red LEDs signaling a faulty operation.

Alternatively, the trigeminal nerve 2 can also be stimulated in a mechanical, electrical, magnetic, thermal and/or chemical fashion by way of the at least one device for acupressure and/or acupuncture described at the outset. The pressure cushions, the various acupuncture needles, the laser or lasers, the herbs and/or the magnetic substance are placed onto the facial skin—or are operated—such that the branch of the trigeminal nerve running to the mandible 5 and/or the branch of the trigeminal nerve running the maxilla 4 is stimulated.

Figure 3:
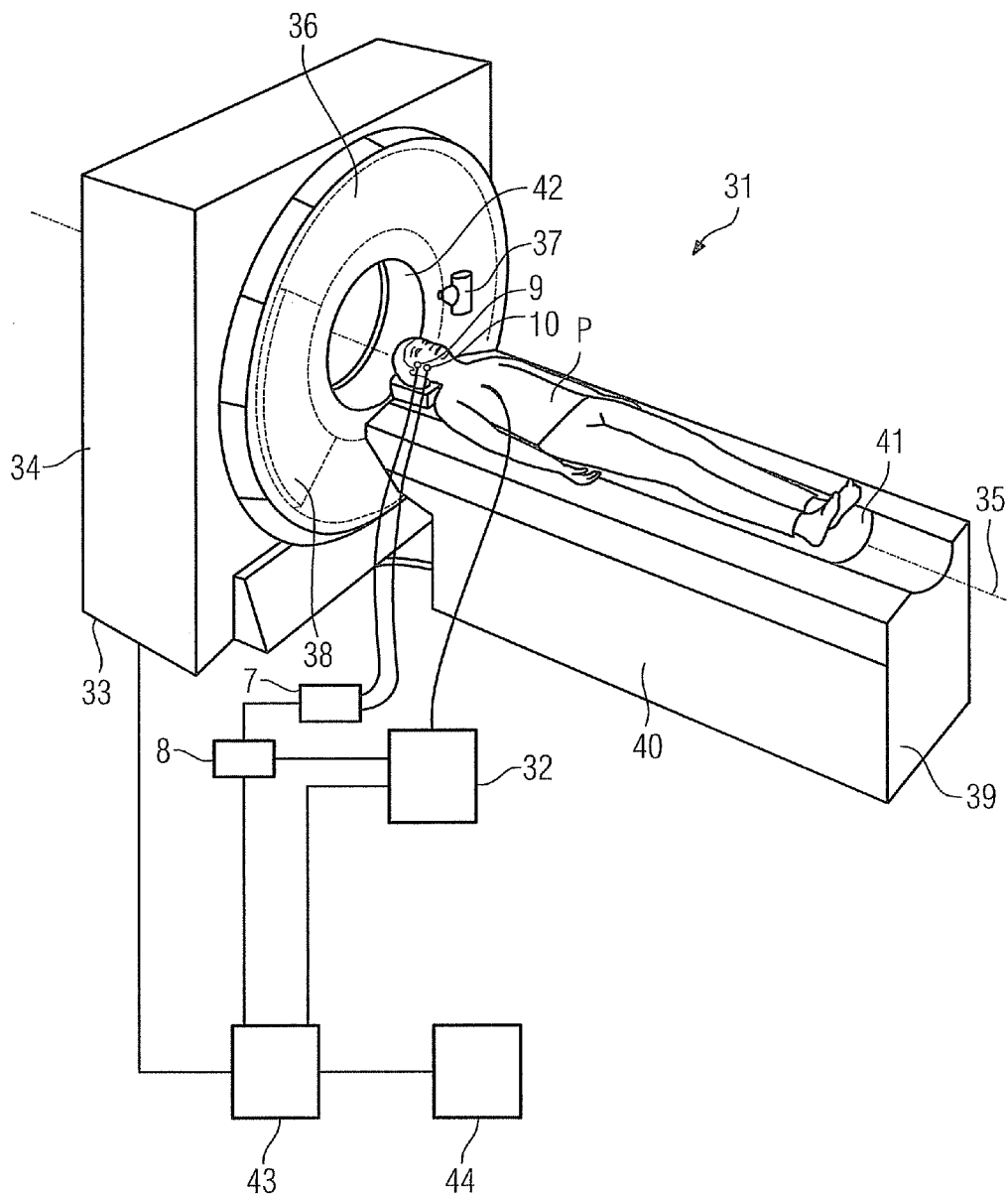
FIG. 3 shows an apparatus, having a device as per FIG. 1, an EKG instrument and an X-ray computed tomography scanner.

The envisaged application of the described devices for stimulating the trigeminal nerve is illustrated in FIG. 3 on the basis of the device shown in FIG. 1. The device from FIG. 1 is part of an apparatus, which, in the case of the present example embodiment of the invention, has an imaging instrument in the form of an X-ray computed tomography scanner and a unit, in the form of an EKG instrument 32, for registering the heart rate of a patient P in addition to the device 6.

The X-ray computed tomography scanner 31 comprises a gantry 33 with a stationary part 34 and with a part 36 that can rotate around a system axis 35. In the case of the present example embodiment of the invention, the rotatable part 36 has an X-ray system, which comprises an X-ray beam source 37 and an X-ray beam detector 38, which are arranged opposite one another on the rotatable part 36. When the X-ray computed tomography scanner 31 is in operation, X-ray radiation emanates from the X-ray beam source 37 in the direction of the X-ray beam detector 38, penetrates a measurement object and is registered by the X-ray beam detector 38 in the form of measurement data or measurement signals.

The X-ray computer tomography scanner 31 moreover has a patient couch 39 for supporting a patient P to be examined. The patient couch 39 comprises a couch base 40, on which a patient support plate 41, provided for actually supporting the patient P, is arranged. The patient support plate 41 can be adjusted in the direction of the system axis 35 relative to the couch base such that said patient support plate can be inserted together with the patient P into the opening 42 of the gantry for recording 2D X-ray projections of the patient P, for example during a helical scan. The mathematical processing of the 2D X-ray projections recorded by the X-ray system, or the reconstruction of slice images, 3D images or a 3D data record on the basis of the measurement data or the measurement signals of the 2D X-ray projections is brought about by a computer 43 of the X-ray computed tomography scanner 31; these slice images or 3D images can be displayed on a display device 44.

In the case of the present example embodiment of the invention, 2D X-ray projections of the heart of the patient P should be recorded from different projection directions during a rest phase of the heart of the patient P in order to reconstruct 2D slice images and/or 3D images of the heart of the patient P. In the process, the heart rate of the patient P should be lowered in a targeted fashion in order to lengthen the rest phase of the heart of the patient for recording the 2D projections.

As already mentioned, use is made here of the device shown in FIG. 1. In the case of the present example embodiment of the invention, the electrodes 9, 10 are arranged on the cheek of the patient P over the main branch of the trigeminal nerve running to the mandible. The control 8 actuates the power-pulse-current generator 7 such that a succession of current pulses is generated that stimulate the main branch of the trigeminal nerve running to the mandible. At the same time, the EKG instrument 32 registers the heart rate of the patient P, and so it is possible to register the heart rate lowered by the stimulation of the trigeminal nerve. The EKG instrument 32 is connected to the control 8, and so the generation of the current pulses on the basis of the measured EKG or on the basis of the measured heart rate can be controlled in a targeted fashion.

Both the control 8 and the EKG instrument 32 are also connected to the computer 43 of the X-ray computed tomography scanner 31, and so the computer 43, depending on the heart rate of the patient P established by the EKG instrument, starts the recording of the 2D X-ray projections of the heart of the patient P when the heart rate has been lowered by stimulating the trigeminal nerve. This affords the possibility of reconstructing high-quality slice images or 3D images of the heart of the patient P on the basis of the recorded 2D X-ray projections.

The trigeminal nerve is generally only stimulated for a brief period of time (less than five minutes, preferably even less than one minute), but this is sufficient for recording sufficiently many 2D X-ray projections of the heart of the patient P.

Incidentally, the electrodes 9, 10 do not necessarily have to be arranged on the cheek of the patient P such that the branch of the trigeminal nerve running to the mandible is stimulated. Rather, the electrodes can also be arranged such that the branch of the trigeminal nerve running to the maxilla is stimulated or that both the branch of the trigeminal nerve running to the maxilla and the branch of the trigeminal nerve running to the mandible are stimulated.

Moreover, the trigeminal nerve can be stimulated on both halves of the face of the patient, for which purpose use is made of at least a second pair of electrodes connected to the power-pulse-current generator 7. Alternatively, provision can be made for a second device 6 in order to be able to stimulate the trigeminal nerve independently on both halves of the face.

In contrast to the example embodiment of the invention shown in FIG. 3, use can also be made of the device 11 or the means for acupressure or the means for acupuncture for stimulating the trigeminal nerve instead of the device 6. Provided that it is sensible, use can simultaneously also be made of a plurality of devices for stimulating the trigeminal nerve.

Incidentally, the imaging instrument need not necessarily be an X-ray computed tomography scanner. Rather, the imaging instrument can also be a C-arm X-ray scanner or a magnetic resonance imaging scanner.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for stimulating a trigeminal nerve of a patient in order to reduce a heart rate of the patient for recording image information from a heart of the patient, comprising:
    at least one device for at least one of mechanical, electrical, magnetic, thermal, optical and chemical stimulation of the trigeminal nerve, the at least one device configured to interact with a unit for registering the heart rate of the patient, wherein the at least one device includes at least one device for exerting mechanical pressure on the trigeminal nerve, the at least one device for exerting mechanical pressure on the trigeminal nerve including at least one balloon, fillable with a medium and arrangeable on an eye of the patient in order to stimulate the branch of the trigeminal nerve running to the eye by exerting pressure on the eye.

2. The device as claimed in claim 1, wherein the at least one balloon is arranged on spectacles, wearable by the patient.

3. The device as claimed in claim 2, wherein the at least one device for exerting pressure on the trigeminal nerve includes at least one of:
    at least one pump for the medium,
    controllable valves for a flow of medium into and from the at least one balloon,
    at least one pressure sensor for establishing a pressure in the balloon, and
    a control unit for actuating the at least one pump.

4. The device as claimed in claim 1, wherein the at least one device for exerting pressure on the trigeminal nerve includes at least one of:
    at least one pump for the medium,
    controllable valves for a flow of medium into and from the at least one balloon, at least one pressure sensor for establishing a pressure in the balloon, and a control unit for actuating the at least one pump.

5. An apparatus, comprising:

the at least one device as claimed in claim 1; and the unit for registering the heart rate of the patient, the unit being configured to interact with the at least one device.

6. The apparatus as claimed in claim 5, further comprising:

an imaging instrument, operatively connected to the unit used to register the heart rate of the patient.

7. The apparatus as claimed in claim 6, wherein the imaging instrument is an X-ray computed tomography scanner, a C-arm X-ray scanner or a magnetic resonance imaging scanner.

8. An apparatus, comprising:

the at least one device as claimed in claim 1; and the unit for registering the heart rate of the patient, the unit being configured to interact with the at least one device.

9. The apparatus as claimed in claim 8, further comprising:

an imaging instrument, operatively connected to the unit for registering the heart rate of the patient.

10. The apparatus as claimed in claim 9, wherein the imaging instrument is an X-ray computed tomography scanner, a C-arm X-ray scanner or a magnetic resonance imaging scanner.

11. A device for stimulating a trigeminal nerve of a patient in order to reduce a heart rate of the patient for recording image information from a heart of the patient, comprising:

at least one device for at least one of mechanical, electrical, magnetic, thermal, optical and chemical stimulation of the trigeminal nerve, the at least one device including at least one device for applying electric current to the trigeminal nerve, the at least one device for applying electric current to the trigeminal nerve including at least one of, at least one pair of electrodes configured to attach to facial skin of the patient, at least one current generator configured to connect to the at least one pair of electrodes, and a control for actuating the at least one current generator.

12. The device as claimed in claim 11, wherein the at least one current generator is a power-pulse-current generator for generating a succession of current pulses.

13. The device as claimed in claim 12, wherein at least one of shape, amplitude, duration and repetition rate of the current pulses are settable.

14. An apparatus comprising:

the at least one device as claimed in claim 11; and the unit for registering the heart rate of the patient, the unit being configured to interact with the at least one device.

15. The apparatus as claimed in claim 14, further comprising:

an imaging instrument, operatively connected to the unit for registering the heart rate of the patient.

16. The apparatus as claimed in claim 15, wherein the imaging instrument is an X-ray computed tomography scanner, a C-arm X-ray scanner or a magnetic resonance imaging scanner.

17. A device for stimulating a trigeminal nerve of a patient in order to reduce a heart rate of the patient for recording image information from a heart of the patient, comprising:

at least one device for at least one of mechanical, electrical, magnetic, thermal, optical and chemical stimulation of the trigeminal nerve, the at least one device configured to interact with a unit for registering the heart rate of the patient, wherein the at least one device includes at least one device for at least one of acupressure and acupuncture for stimulating the trigeminal nerve.

18. A method for reducing a heart rate of a patient in order to record image information from a heart of the patient, the method comprising:

stimulating a trigeminal nerve of the patient, at least one of mechanically, electrically, magnetically, thermally, optically and chemically, in order to lower the heart rate of the patient, wherein stimulating the trigeminal nerve includes at least one of, exerting pressure on at least one eye of the patient by way of a balloon filled with a medium, applying current pulses to the trigeminal nerve, and stimulating the trigeminal nerve with at least one device for acupuncture.

19. A method for reducing a heart rate of a patient in order to record image information from a heart of the patient, the method comprising:

stimulating a trigeminal nerve of the patient, at least one of mechanically, electrically, magnetically, thermally, optically and chemically, in order to lower the heart rate of the patient, wherein the trigeminal nerve is stimulated by at least one device for at least one of mechanical, electrical, magnetic, thermal, optical and chemical stimulation of the trigeminal nerve, and the stimulating the trigeminal nerve includes at least one of, exerting pressure on at least one eye of the patient by way of a balloon filled with a medium;

applying current pulses to the trigeminal nerve, and stimulating the trigeminal nerve with at least one device for acupuncture.

20. A method for reducing a heart rate of a patient in order to record image information from a heart of the patient, the method comprising:

stimulating a trigeminal nerve of the patient, at least one of mechanically, electrically, magnetically, thermally, optically and chemically, in order to lower the heart rate of the patient, the stimulating being performed at least one device for exerting mechanical pressure on the trigeminal nerve, the at least one device for exerting mechanical pressure on the trigeminal nerve including at least one balloon, fillable with a medium and arrangeable on an eye of the patient in order to stimulate the branch of the trigeminal nerve running to the eye by exerting pressure on the eye; and interacting with a unit for registering the heart rate of the patient.

21. The method as claimed in claim 20, wherein the heart rate of the patient is monitored by the unit for registering the heart rate of the patient during the stimulation of the trigeminal nerve.

22. The method as claimed in claim 20, wherein image information from the heart of the patient is recorded by an imaging instrument during the stimulation of the trigeminal nerve.

23. The method as claimed in claim 20, wherein the heart rate of the patient is monitored by the unit for registering the heart rate of the patient during the stimulation of the trigeminal nerve.

24. The method as claimed in claim 20, wherein image information from the heart of the patient is recorded by an imaging instrument during the stimulation of the trigeminal nerve.

25. A non-transitory computer readable medium including program segments for, when executed on a computer device, causing the computer device to implement the method of claim 20.

26. A non-transitory computer readable medium including program segments for, when executed on a computer device, causing the computer device to implement the method of claim 20.

\* \* \* \* \*